Aug. 16, 1949. R. L. BYRUM Plant Pat. 864

ROSE PLANT

Filed Oct. 29, 1947

Inventor.
Roy L. Byrum
By Robb & Robb
Attorneys

Patented Aug. 16, 1949

Plant Pat. 864

UNITED STATES PATENT OFFICE

864

ROSE PLANT

Roy L. Byrum, Richmond, Ind., assignor to Joseph H. Hill Company, Richmond, Ind., a corporation of Indiana Application October 29, 1947, Serial No. 782,889

1 Claim. (Cl. 47—61)

The present invention relates to a new and distinct variety of rose plant, originating as a cross of two unnamed seedling varieties, having as its primary object to improve the color of the flowers.

In this particular instance, I used as the seed parent a seedling of medium red color coming from the cross of "Lucile Hill" (Pl. Pat. No. 305) and "Chieftain" (Pl. Pat. No. 150), and as the pollen parent a large, dark pink seedling, the result sought being to improve the coloring of the flowers of the seed parent while retaining the other good qualities.

I succeeded in obtaining the color improvement of the flowers referred to, in combination with other novel characteristics in relation to the foliage.

Since "Better Times" (Pl. Pat. No. 23) is such a well-known variety, comparison of this new rose with it may be made. As to the color of the flowers, where the chief difference resides, "Better Times" is dark pink or cerise, while the new rose is Carmine to Spectrum Red. As to the leaflets, those on the present rose are long and narrow, except as to the end one as seen in the drawings; all "Better Times" leaflets are broad and are simply serrated and ovoid where those of the new rose are more deeply serrated and are irregularly serrated with only the end one ovoid in shape.

Asexual reproduction of this new variety shows the foregoing characteristics come true to form and are established.

In the drawing:

Fig. 1 shows a specimen of the bud as the calyx breaks;

Fig. 2 shows the bud as the first pedal opens;

Fig. 3 shows the bloom when full blown;

Fig. 5 is another specimen of the foliage (under surface); and

Fig. 6 is a section of the stem.

Figure 4:
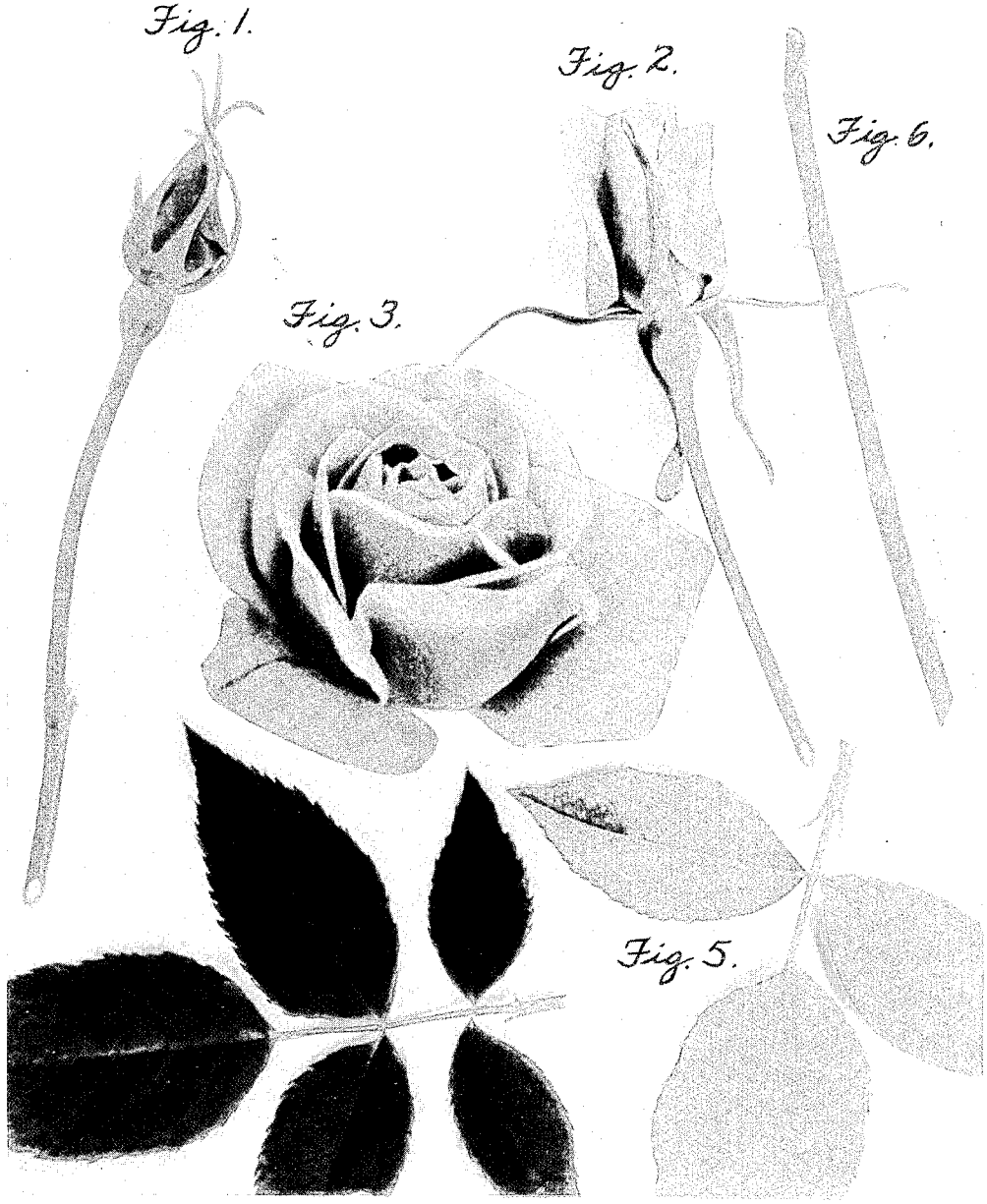
Fig. 4 is a specimen of the foliage (upper surface)

(All figures of the original drawing are made to the same scale.)

The following is a detailed description of the new variety, color terminology being in accordance with Ridgway's Color Standard, except where otherwise indicated to have ordinary dictionary significance:

Type: Greenhouse; seedlings; for cut flowers.

Class: Hybrid tea.

Breeding: Seedling.

*Seed parent.*—Unnamed seedling.

*Pollen parent.*—Unnamed seedling.

Propagation: Holds its distinguishing characteristics through succeeding propagations by grafting, budding, and cutting.

*Flower*

Locality where grown: Richmond, Indiana.

Flowers borne: Singly to stem on normal, strong, medium long stems.

Quantity of bloom: Abundant in greenhouse.

Continuity: Continuous.

Fragrance: Moderate; tea.

Bud:

*Peduncle.*—Short; medium heavy; erect; light green; almost smooth; few hairs.

*Before calyx breaks.* — *Size* — medium. *Form*—short; pointed, with a conspicuous neck; with foliaceous appendages on the surface of the bud; with bristlelike foliaceous parts extending beyond the tip of the bud equal to ¼ or more of its length.

*As calyx breaks.*—*Color*—Victoria Lake, Plate 1.

*As first petal opens.*—*Size*—medium. *Form*—long; pointed. *Color*—outside; Carmine, Plate 1, tinted with Ox-blood Red, Plate 1; inside; Velvet Red; between Spectrum Red, Plate 1, and Carmine, Plate 1.

*Opening.*—Opens up well.

Bloom: Size, when fully open, medium large; 3" to 4".

*Petalage.*—Very double; from 35 to 40 petals arranged regularly.

*Form.*—Cupped at first; petals remaining at first very tightly rolled outward; becoming later, at maturity, loosely rolled outward.

Petals: Leathery; with inside satiny and outside shiny.

*Shape.*—Outside—obovate. Intermediate—obovate. Inside—oblong; ruffled.

This description of a newly opened flower was made from a rose grown in a greenhouse in the month of November, at Richmond, Indiana:

*Color.*—*Outside petal*—outside surface: Carmine, Plate 1; inside surface: Spectrum Red, Plate 1, washed with Carmine, Plate 1. *Intermediate petal*—outside surface: Carmine, Plate 1; inside surface: Spectrum Red, Plate 1, washed with Carmine, Plate 1. *Inner petal*—outside surface: Carmine, Plate 1; inside surface: Spectrum Red, Plate 1, washed with Carmine, Plate 1.

This description was made from a rose that was open for three days in a greenhouse in the month of November, at Richmond, Indiana:

*Color.*—*Outside petal*—outside surface: between Carmine, Plate 1, and Spectrum Red, Plate 1; inside surface: Spectrum Red, Plate 1. *Inside petal*—outside surface: between Carmine, Plate 1, and Spectrum Red, Plate 1; inside surface: Spectrum Red, Plate 1.

*General color effect.*—Newly opened flower—Carmine, Plate 1. Three days open—Spectrum Red, Plate 1.

*Behavior.*—Persist.

*Flower longevity.*—Cut roses grown in greenhouse kept at living-room temperatures—three to four days in November.

*Reproductive organs*

Stamens: Many, arranged regularly about pistils.
Filaments: Medium length; reddish, most with anthers.
Anthers: Small; yellow; all open at once.
Pollen: Abundant; gold.
Pistils: Medium number.
Styles: Very uneven; short; thin; bunched.
Stigma: White.
Ovaries: All enclosed in calyx.
Sepals: Permanent; moderate length; spear-shaped. *Color*—inside: Light Lumiere Green, Plate XVII; outside: Light Bice Green, Plate XVII.

*Plant*

Foliage:

*Leaves.*—Compound of five leaflets; abundant; medium large; leathery.

*Leaflets.* — Shape — ovoid - lanceolate with apex acute. Base—acute. Margin—Doubly irregularly serrate.

*Color.*—*Mature*—upper surface: very dark green; under surface: light green. *Young*—upper surface: light green bronze; under surface: moderately bronze.

*Rachis.*—Heavy; grooved; extremely smooth.

*Stipules.*—Medium long; very narrow; with very short points turning out at an angle of less than 45°.

*Disease.*—Resistant to mildew and blackspot.

Growth:

*Habit.*—Bush; upright; much branched.

*Growth.*—Vigorous.

*Canes.*—Medium heavy.

*Main stems.*—Dull bronze. *Thorns*—few; short; hooked downward; with short, narrow base. *Prickles and hairs*—none.

*Branches.*—Bright green. *Thorns*—few; short; hooked downward; with short, narrow base. *Prickles and hairs*—none.

*New shoots.*—Dull green bronze. *Thorns*—few; short; hooked downward; with short, narrow base. *Prickles and hairs*—none.

I claim:

A new and distinct variety of rose plant characterized as to novelty by the coloring of its flowers and shape of foliage, substantially as shown and described.

ROY L. BYRUM.

No references cited.